United States Patent
Durot et al.

(10) Patent No.: US 9,518,144 B2
(45) Date of Patent: Dec. 13, 2016

(54) MASKED POLYISOCYANATE AND USES THEREOF

(71) Applicant: SOPREMA, Strasbourg (FR)

(72) Inventors: Louis Durot, Paris (FR); Pierre-Etienne Bindschedler, Obernai (FR); Virginie Francois Barseghian, Paris (FR); Remi Perrin, Boersch (FR)

(73) Assignee: Soprema, Strasbourg (FR)

(*) Notice: Subject to any disclaimer, the term of this patent is extended or adjusted under 35 U.S.C. 154(b) by 85 days.

(21) Appl. No.: 14/352,027

(22) PCT Filed: Oct. 18, 2012

(86) PCT No.: PCT/FR2012/052372
§ 371 (c)(1),
(2) Date: Apr. 15, 2014

(87) PCT Pub. No.: WO2013/057430
PCT Pub. Date: Apr. 25, 2013

(65) Prior Publication Data
US 2014/0243484 A1    Aug. 28, 2014

(30) Foreign Application Priority Data
Oct. 20, 2011  (FR) ...................... 11 59492

(51) Int. Cl.
| | |
|---|---|
| C08G 18/64 | (2006.01) |
| C08L 95/00 | (2006.01) |
| C08G 18/80 | (2006.01) |
| C08G 18/70 | (2006.01) |
| C07C 265/14 | (2006.01) |
| C07C 271/20 | (2006.01) |
| C07C 271/28 | (2006.01) |

(52) U.S. Cl.
CPC ......... *C08G 18/6415* (2013.01); *C07C 265/14* (2013.01); *C07C 271/20* (2013.01); *C07C 271/28* (2013.01); *C08G 18/80* (2013.01); *C08L 95/00* (2013.01)

(58) Field of Classification Search
None
See application file for complete search history.

(56) References Cited

U.S. PATENT DOCUMENTS

| | | | | |
|---|---|---|---|---|
| 4,559,397 A * | 12/1985 | Noll | ................ | C08G 18/10 427/385.5 |
| 4,795,760 A | 1/1989 | Lucke | | |
| 4,871,792 A | 10/1989 | Lucke | | |
| 5,210,127 A * | 5/1993 | Werner | ............... | C08G 18/0871 521/131 |
| 5,219,979 A | 6/1993 | Greco | | |
| 5,319,008 A | 6/1994 | Janoski | | |
| 5,369,207 A | 11/1994 | Wolff et al. | | |
| 5,441,808 A * | 8/1995 | Anderson | ............... | C08G 18/10 428/349 |
| 5,455,374 A * | 10/1995 | Seneker | ............... | C08G 18/758 560/330 |
| 6,060,574 A | 5/2000 | Schmalstieg et al. | | |
| 9,365,743 B2 * | 6/2016 | Durot | .................. | C08G 18/289 |

(Continued)

FOREIGN PATENT DOCUMENTS

| | | |
|---|---|---|
| AU | 20324/88 | 2/1990 |
| EP | 1 108 735 A1 | 6/2001 |
| EP | 1 798 248 A1 | 6/2007 |
| EP | 2 383 304 A1 | 11/2011 |
| GB | 2 242 435 A | 10/1991 |
| WO | 02/051901 A1 | 7/2002 |
| WO | 2010/106022 A1 | 9/2010 |

OTHER PUBLICATIONS

Carter, N.G. "Oxazolidine Diluents: Reacting for the environment", Surface Coatings International (2009), vol. 82(10), pp. 497-502.
The International Search Report for PCT/FR2012/052372 dated Jan. 25, 2013.

*Primary Examiner* — Randy Gulakowski
*Assistant Examiner* — Christopher M Rodd
(74) *Attorney, Agent, or Firm* — McDonnell Boehnen Hulbert & Berghoff

(57) ABSTRACT

The invention relates to polyurethane resin compositions and, in particular, stable, ready-to-use polyurethane resin compositions comprising: a masked polyisocyanate having formula (I), wherein B represents alkyl and A represents a group comprising a number of isocyanate functions of between 1.5 and 2.2, preferably between 1.5 and 2.1 and, more preferably, between 1.5 and 2; or a masked pre-polymer that is the product of a reaction between the above-mentioned masked polyisocyanate and a polyol having between 1.5 and 3 OH functions and a molecular mass of between 900 and 3,000 g/mol, in a ratio such that the number of NCO functions of the masked polyisocyanate in relation to the number of OH functions of the polyol is between 1.5 and 2.5 approximately; or a mixture of the aforementioned masked polyisocyanate and masked pre-polymer. The invention also relates to the use of the masked polyisocyanate in order to form a masked pre-polymer by reacting said masked polyisocyanate on a polyol, and to the use of a masked polyisocyanate and/or a masked pre-polymer in polyurethane resin compositions.

(I)

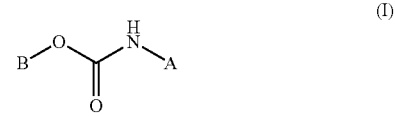

13 Claims, No Drawings

(56) References Cited

U.S. PATENT DOCUMENTS

| | | |
|---|---|---|
| 2003/0022965 A1 | 1/2003 | Durot et al. |
| 2003/0134127 A1 | 7/2003 | Konig et al. |
| 2010/0105829 A1 | 4/2010 | Schmatloch |
| 2010/0152381 A1 | 6/2010 | Savino et al. |
| 2014/0249263 A1* | 9/2014 | Durot .................... C07C 271/06 524/507 |

* cited by examiner

MASKED POLYISOCYANATE AND USES THEREOF

This application is a U.S. national phase of International Application No. PCT/FR2012/052372, filed Oct. 18, 2012, the disclosure of which is hereby incorporated by reference in its entirety.

FIELD OF APPLICATION

The present invention discloses a masked polyisocyanate which makes it possible to satisfy the ecological requirements in terms of free diisocyanate monomers emission. This compound is intended to be introduced in a polyurethane resin composition, especially in a stable one-component polyurethane resin composition, so as to bring the free diisocyanate monomers content to a compliant level below the regulations in force. This compound is also intended to react with a polyol so as to form a masked prepolymer which may also be introduced into a polyurethane resin composition, especially into a stable one-component polyurethane resin composition, so as to bring the free diisocyanate monomers content to a compliant level below the regulations in force. Furthermore, the masked polyisocyanate and the masked prepolymer according to the invention are advantageously less reactive than standard polyisocyanates and prepolymers, which makes it possible to improve the stability of the compositions on storage. What is more, the masked polyisocyanate is a good compatibilizer for the hydrocarbon fillers and prepolymers present in non-bituminous polyurethane resin compositions and bituminous polyurethane resin compositions, preferably stable one-component compositions.

PRIOR ART

Polyurethane resins are very useful in many fields, in particular in public works or construction works, where they make it possible to form coatings applied onto structures, especially to provide waterproofness or protection thereto.

Conventionally, a polyurethane resin comprises a prepolymer, which is the reaction product of a diisocyanate and/or polyisocyanate with one and/or more polyols, a solvent and/or diluent, optionally a catalyst for accelerating the polymerization and optionally a compatibilizer and a filler. The compatibilizer is necessarily present when the resin is a bituminous resin or is intended to be applied onto a bituminous coating.

However, these compositions containing diisocyanates may be considered as harmful to health and to the environment since they may release free diisocyanate monomers, i.e. monomers that are not attached to the prepolymer. Thus, the regulation of certain States only permits a free diisocyanate monomers content of less than 1% in a final polyurethane resin composition, which is preferably a stable one-component composition.

The present inventors have found that it is possible to reduce, or even eliminate, the free diisocyanate monomers by means of a polyisocyanate masked with a monoalcohol and/or by means of a masked prepolymer. Thus, the present invention relates to liquid polyurethane resin compositions containing a polyisocyanate masked with a monoalcohol and/or a masked prepolymer, which are stable and non-toxic since they have a free diisocyanate monomers content that is compliant with the regulatory requirements, to the use of the masked polyisocyanate for forming masked prepolymers and also to the use of a masked polyisocyanate and/or of a masked prepolymer in a polyurethane resin composition.

DEFINITIONS

According to the present invention, the term "liquid composition" means a composition with a viscosity between 1,000 and 40,000 centipoises, said viscosity being measured at 23° C. using a Brookfield viscometer (for viscosities of less than 10,000 centipoises, the measurements are taken with the R5 module at a speed of 30 rpm and for viscosities of greater than 10,000 centipoises, the measurements are taken with the R6 module at a speed of 20 rpm. Such a viscosity allows the application of the composition especially with a roller commonly known as a "pile roller" or a brush to form 0.5 to 2 mm thick layers in a single application.

The term "one-component composition" or "ready-to-use composition" means a composition which is intended to be applied on its own by the final user, i.e. by the worker who will produce the waterproof coating. Such a ready-to-use composition is conventionally known in the art as a "one-component" composition, as opposed to compositions which require the addition of a catalyst or hardener or other reactive agent before use or which must be applied in a limited time span (a few hours) after being mixed.

The term "stable composition" means a composition which can be stored for a minimum of 4 months without any phase separation or mass gelling being observed.

The term "non-toxic composition" means a polyurethane resin composition or bituminous polyurethane resin composition which contains less than 1% by weight of free diisocyanate monomers, according to directive 67/548/EEC (30th ATP directive 2008/58/EC), the free diisocyanate monomer content being measured by gas chromatography coupled to a mass spectrometer (according to standard EN ISO 17734-1/2006).

The term "prepolymer" means a reaction product of a polyol or of a mixture of polyols containing a number of OH functions between 1.5 and 3 with a polyisocyanate or a mixture of polyisocyanates containing a number of NCO functions between 1.6 and 3, in a ratio such that the number of NCO functions of the polyisocyanate or of the polyisocyanate mixture relative to the number of OH functions of the polyol or mixture of polyols is from 1.5 to 2.5 approximately.

The term "polyisocyanate" means a compound containing more than one isocyanate function; the diisocyanate may therefore also be termed in the present application a polyisocyanate.

The term "TDI" means toluene diisocyanate.
The term "MDI" means diphenylmethane diisocyanate.
The term "HDI" means hexamethylene diisocyanate.
The term "IPDI" means isophorone diisocyanate.

The term "alkyl" means a hydrocarbyl radical containing 2 to 20 carbon atoms, corresponding to the general formula $C_nH_{2n+1}$ wherein n is greater than or equal to 2. The alkyl groups may be linear or branched and may be substituted with unreactive groups chosen from halogen, alkyl, cycloalkyl, heterocycloalkyl, arylcycloalkyl, heteroarylcycloalkyl, aryl, heteroaryl, alkoxy, haloalkyl, arylalkyl, heteroarylalkyl and hydrocarbyl containing at least one unsaturation.

The term "aryl" means a polyunsaturated aromatic hydrocarbyl group containing only one ring (i.e. phenyl) or several fused rings (for example naphthyl) or several rings linked via a covalent bond (for example biphenyl), which typically contain 5 to 12 and preferentially 6 to 10 carbon atoms, and wherein at least one ring is aromatic. The aromatic ring may optionally comprise one to two additional fused rings (i.e. cycloalkyl, heterocycloalkyl or heteroaryl). The term "aryl" also comprises partially hydrogenated derivatives of carbocyclic systems described above.

When the suffixes "ene" or "diyl" are used in conjunction with an alkyl group, this means that the alkyl group defined above contains two single bonds as points of attachment to other groups.

The term "arylalkyl" or "heteroarylalkyl" means a linear or branched alkyl substituent containing a carbon atom attached to an aryl or heteroaryl ring.

The term "heteroaryl" means one ring or two rings that are fused or linked via a covalent bond, comprising 5 to 12 carbon atoms and preferentially 5 to 6 carbon atoms, wherein at least one of the rings is aromatic and wherein at least one or more carbon atoms are replaced with oxygen, nitrogen and/or sulfur. The nitrogen and/or sulfur atoms may optionally be oxidized and the nitrogen atom may optionally be quaternized. The term "heteroaryl" also comprises systems described above containing a fused aryl, cycloalkyl, heteroaryl or heterocycloalkyl group.

The term "cycloalkyl" means a saturated or unsaturated, cyclic monovalent hydrocarbyl, containing one or 2 rings and comprising 3 to 10 carbon atoms.

The term "heterocycloalkyl" means a cycloalkyl wherein at least one carbon atom is replaced with an oxygen, nitrogen and/or sulfur atom.

The term "arylcycloalkyl" or "heteroarylcycloalkyl" means a cycloalkyl that is fused or linked via a covalent bond to an aryl or heteroaryl ring.

The term "arylheterocycloalkyl" or "heteroarylheterocycloalkyl" means a heterocycloalkyl that is fused or linked via a covalent bond to an aryl or heteroaryl ring.

The term "hydrocarbyl" means a hydrocarbon chain containing 2 to 30 carbon atoms.

The following groups: alkyl, aryl, arylalkyl, arylcycloalkyl, arylheterocycloalkyl, heteroaryl, heteroarylalkyl, hydrocarbyl with at least one unsaturation, may also comprise one or more standard substituents chosen from halogen, alkyl, cycloalkyl, heterocycloalkyl, aryl, heteroaryl, alkoxy, haloalkyl and arylalkyl.

Masked Polyisocyanate

The masked polyisocyanate used in the present invention is a polyisocyanate in which a NCO function has been masked with a monoalcohol, i.e. an adduct of polyisocyanate and of monoalcohol, the two components being linked together via a urethane bond.

This masked polyisocyanate is an alkyl monourethane of polyisocyanate having a number of isocyanate functions between 1.5 and 2.2, preferably between 1.5 and 2.1 and even more preferentially between 1.5 and 2.

The masked polyisocyanate introduced in the composition according to the invention has the following formula:

$$B-O-\underset{\underset{O}{\parallel}}{C}-\underset{H}{N}-A$$

wherein:
B represents alkyl,
A represents a group comprising a number of isocyanate functions between 1.5 and 2.2, preferably between 1.5 and 2.1 and even more preferentially between 1.5 and 2.

The number of isocyanate functions is estimated by calculation after NCO titration by back-titrating the excess of dibutylamine with hydrochloric acid (according to standard EN ISO 14896-2006).

Preferably, B is an optionally unsaturated $C_2$-$C_{20}$, preferably $C_3$-$C_{12}$ and even more preferentially $C_4$-$C_{10}$ alkyl.

Preferably, the "group" of A is:

a polymer chain (originating from a polymeric MDI) corresponding to formula (A1):

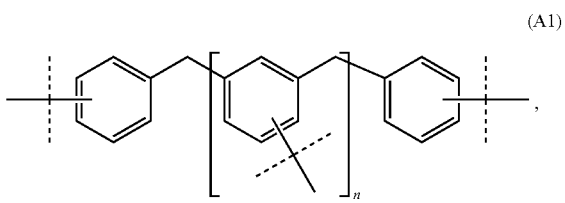

(A1)

a radical corresponding to formula (A2) or to a related radical of a TDI trimer:

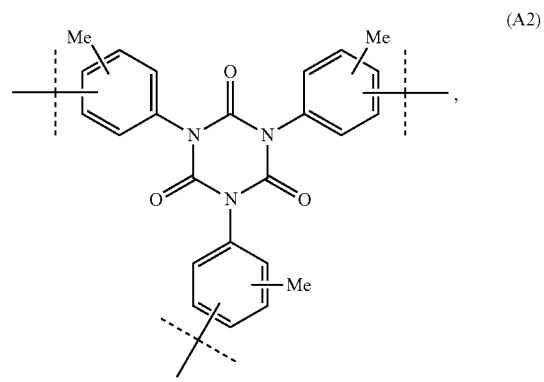

(A2)

a radical corresponding to one of the formulae (A3) and/or (A4) or to a related radical of a HDI trimer:

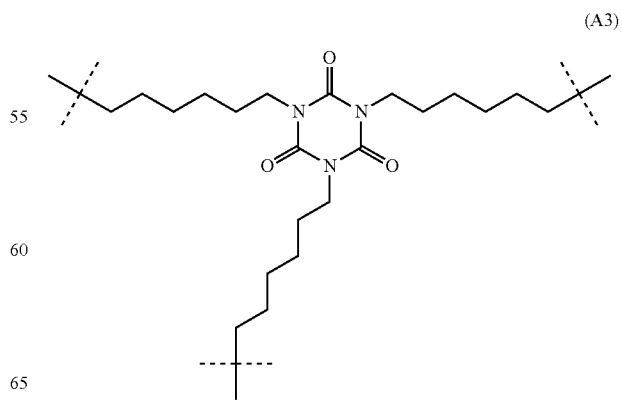

(A3)

(A4)

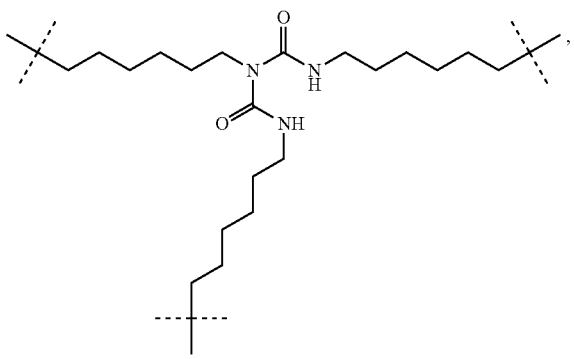

a radical corresponding to formula (A5) or to a related radical of an IPDI trimer:

(A5)

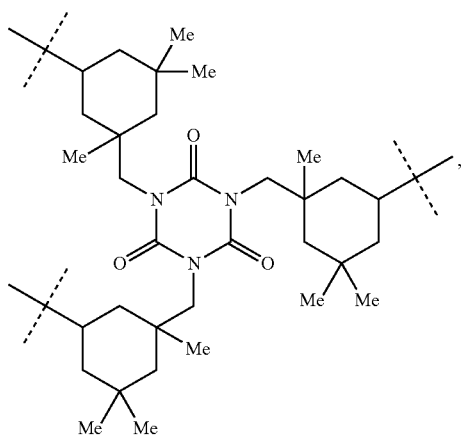

wherein each dashed line represents a point of attachment to a NCO function or to the group —NHCOO—B of the masked polyisocyanate and on condition that there is at least one dashed line that is a point of attachment to the group —NHCOO—B and that the remaining lines represent a point of attachment to a NCO function.

The masked polyisocyanate may be prepared via a process which comprises the gradual addition of a monoalcohol of formula B—OH to a polyisocyanate of formula A-NCO, A and B being as defined above.

The monoalcohol enabling the masking may be an aliphatic $C_2$-$C_{20}$, preferably $C_3$-$C_{12}$ and even more preferentially $C_4$-$C_{10}$ monoalcohol.

Advantageously, the monoalcohol is chosen from the group comprising hexanol, 2-ethylhexanol, methylhexanol, butanol and terpenols, and mixtures thereof.

The polyisocyanate used to form the masked polyisocyanate is aromatic, aliphatic or cycloaliphatic and comprises between 2.5 and 3.2 NCO functions. It may be chosen from the group comprising a toluene diisocyanate (TDI) trimer, a polymeric diphenylmethane diisocyanate (MDI), a hexamethylene diisocyanate (HDI) trimer and an isophorone diisocyanate (IPDI) trimer, and mixtures thereof.

Preferably, the polyisocyanate used to form the masked polyisocyanate is a polymeric MDI containing between 2.5 and 3.2 NCO functions or a TDI trimer.

More particularly, to form the masked polyisocyanate, an aromatic polyisocyanate that may be used is a polymeric MDI containing 2.7 isocyanate functions, such as Suprasec® 5025 sold by Huntsman or a polymeric MDI containing 2.9 isocyanate functions, such as Suprasec® 2085 sold by Huntsman.

An example of an aliphatic polyisocyanate that may be used to form the masked polyisocyanate is a HDI trimer containing approximately 3 isocyanate functions, such as Desmodur® N3300 or Desmodur® N100 sold by Bayer.

In order to obtain a number of isocyanate functions between 1.5 and 2.2 on the masked polyisocyanate, 0.60 mol to 1.50 mol and preferably 0.80 mol to 1.3 mol of monoalcohol are added per 1 mol of polyisocyanate. If the monoalcohol content is too low, the number of isocyanate functions will be greater than 2.2, and the mechanical properties, especially the elasticity, of the coating obtained using a composition containing this masked polyisocyanate would be impaired.

The masking of the polyisocyanate predominantly takes place on the most reactive isocyanate function. As a result, the reactivity of the masked polyisocyanate is reduced, which enables the compositions containing it to be more stable over time than compositions containing a nonmasked polyisocyanate. Furthermore, the use of the masked polyisocyanate improves the compatibilization between the prepolymers and the bituminous mixtures using natural or synthetic bitumens, especially in stable one-component bituminous polyurethane resin compositions.

The reaction between the monoalcohol and the polyisocyanate is an exothermic reaction. The gradual addition of the monoalcohol is thus controlled so as to limit the temperature increase to a value below 60° C., preferably below 50° C. and even more preferentially below 40° C.

When the temperature returns to room temperature (about 20° C.), the reaction is complete.

This process is environmentally friendly, given that it is performed in the absence of any solvent and without heating and that it does not generate any toxic vapors.

Polyurethane Composition

A first object of the invention is a polyurethane resin composition, preferably a stable one-component polyurethane resin composition, whose free diisocyanate monomers content is compliant with the regulatory requirements and whose reactivity is controlled.

This composition may be a one-component polyurethane resin composition or alternatively part of a multi-component polyurethane resin composition, more particularly the isocyanate part of a two-component composition, the other part conventionally comprising a polyol.

Preferably, the polyurethane resin composition according to the invention is not a polyurethane foam composition. As a result, according to a particular embodiment, the composition according to the invention will not be mixed with water to polymerize and give a polyurethane foam. Similarly, the composition according to the invention is not intended to be mixed with a blowing agent, such as a gas, for example propane, butane, isobutane, carbon dioxide, carbon monoxide or dimethyl ether to form a polyurethane foam.

One object of the invention is thus a polyurethane resin composition, preferably a stable one-component composition, and even more preferentially a non-toxic stable one-component composition, which comprises:
  at least one masked polyisocyanate as defined previously;
  at least one prepolymer;
  optionally a plasticizer;
  optionally a catalyst;

optionally solvent and/or diluent;
optionally fillers.

The prepolymer (referred to hereinbelow as the standard prepolymer) may also be replaced with a mixture of a prepolymer with a masked prepolymer.

It is important to point out that the composition according to the invention comprises the masked polyisocyanate per se, and not reagents for forming the masked polyisocyanate. Thus, the masked polyisocyanate must be presynthesized before being introduced into the composition. Indeed, if a monoalcohol, a polyisocyanate containing between 2 and 3.2 NCO functions and a prepolymer are introduced in a polyurethane resin composition, the prepolymer will react with the monoalcohol, which is not desirable for obtaining an elastic coating since the polymerization will be stopped at the end of the chain because the prepolymer will have no more reactive functions once it has been partially neutralized by the monoalcohol. The resulting polymer chains will therefore be shorter, which is detrimental to the elasticity and to the strength of the final coating.

It is also important to point out that the masking of the polyisocyanate is partial masking, i.e. free NCO functions remain to react with OH and/or NCO functions. Partial masking of the polyisocyanate differs from total masking, wherein all the NCO functions of the polyisocyanate are masked. Indeed, the masked polyisocyanate according to the invention can still polymerize or react with a prepolymer via a urea bond, whereas a fully masked polyisocyanate is not free to polymerize, and a thermal or chemical means needs to be used in order to deblock some of the NCO functions before the composition can polymerize. Total masking of the NCO functions of a polyisocyanate followed by demasking via a thermal or chemical means does not apply to the compositions envisioned herein. Thus, in the compositions according to the invention, there is no need, for example, to heat the composition to high temperature in order to release the masked NCO functions or to add a chemical compound which would make it possible to demask the masked NCO functions to initiate the polymerization.

The prepolymer used in the composition according to the invention may be a prepolymer conventionally used in polyurethane compositions (referred to hereinbelow as a standard prepolymer) or a masked prepolymer.

A masked prepolymer is the reaction product of a polyol with the masked polyisocyanate having a number of isocyanate functions between 1.5 and 2.2 as described above or of a polyol with a mixture of a polyisocyanate and a masked polyisocyanate having a number of isocyanate functions between 1.5 and 2.2 as described above.

Standard prepolymers are formed by reaction between:
a polyol containing between 1.5 and 3 OH functions; and
a standard diisocyanate and/or polyisocyanate containing between 1.6 and 3 NCO functions;
in a ratio such that the number of NCO functions of the polyisocyanate or of the mixture of polyisocyanates relative to the number of OH functions of the polyol or mixture of polyols is from 1.5 to 2.5 approximately.

The polyol used to form the standard prepolymer may be of polyether type such as a polyethylene glycol (PEG), a polypropylene glycol (PPG), a polypropylene glycol glycerol triol, or a polytetrahydrofuran (PTHF) or a polyester type polyol, such as Priplast® 3196 sold by Croda or Krasol® LBH-p 3000 sold by Cray Valley or a polycaprolactone such as PCP 1000 sold by Solvay.

The standard diisocyanate and/or polyisocyanate used to form the standard prepolymer may especially be MDI, a polymeric MDI, TDI, a TDI trimer, HDI, a HDI trimer, IPDI, an IPDI trimer, and mixtures thereof.

Preferably, the standard diisocyanate and/or polyisocyanate used to form the standard prepolymer is MDI, a polymeric MDI, TDI, a TDI trimer, and mixtures thereof.

Examples that may be used include a standard prepolymer resulting from the reaction of a standard polyisocyanate such as MDI with a polyether, such as polypropylene glycol (PPG) or polytetrahydrofuran (PTHF); or with a polyester, such as Priplast® 3196 sold by Croda or Krasol® LBH-p 3000 sold by Cray Valley.

The catalyst that may be introduced into the composition according to the invention is a catalyst conventionally used in polyurethane compositions. Examples that may be used include organometallic catalysts based on bismuth, vanadium or tin, such as dibutyltin dilaurate, or on tertiary amines, such as Jeffcat® DMDLS sold by Huntsman.

The fillers that may be introduced into the present composition are liquid fillers which are aromatic plasticizing oils and exogenous plasticizers such as diisopropylnaphthalene, dioctyl phthalate (DOP), diisononyl phthalate (DINP), Mesamoll®, trimethylpentanediol diisobutyrate (TXIB) and butylbenzyl phthalate, natural or synthetic bitumens or a liquid bituminous mixture also known as a "cut-back", and solid fillers such as pigments, calcium carbonate, titanium oxide, or the like.

The composition according to the invention may be stable one-component liquid or intended to be mixed before use.

According to a particular embodiment, this composition does not contain the masked polyisocyanate per se but at least part of the prepolymer is a masked prepolymer which is the reaction product of a polyol with the masked polyisocyanate having a number of isocyanate functions between 1.5 and 2.2 as described above.

Thus, another object of the invention is a polyurethane composition which comprises:
at least one masked prepolymer formed by reaction between:
a polyol containing between 1.5 and 3 OH functions and having a molecular weight between 900 and 3,000 g/mol, preferably between 1,000 and 2,800 g/mol and more preferentially between 1,500 and 2,500 g/mol, and
a masked polyisocyanate corresponding to the following formula

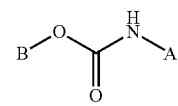

wherein:
B represents alkyl,
A represents a group comprising a number of isocyanate functions between 1.5 and 2.2, preferably between 1.5 and 2.1 and even more preferentially between 1.5 and 2;
in a stoichiometric molecular ratio of from 1.5 to 2.5 approximately of masked polyisocyanate relative to the polyol;
optionally a polyisocyanate containing between 1.5 and 3 NCO functions;
optionally a plasticizer;
optionally a catalyst;
optionally solvent and/or diluent.

According to another particular embodiment, the composition according to the invention comprises both the masked polyisocyanate and at least part of the prepolymer is a masked prepolymer which is the reaction product of:
- a polyol containing between 1.5 and 3 OH functions and having a molecular weight between 900 and 3,000 g/mol, preferably between 1,000 and 2,800 g/mol and more preferentially between 1,500 and 2,500 g/mol; with
- a masked polyisocyanate containing a number of isocyanate functions between 1.5 and 2.2 as described previously;

in a ratio such that the number of NCO functions of the polyisocyanate relative to the number of OH functions of the polyol is from 1.5 to 2.5 approximately.

Said polyol containing between 1.5 and 3 OH functions and having a molecular weight between 900 and 3,000 g/mol used to form the masked prepolymer may be a polyether, polyester, polybutadiene or polycarbonate type polyol, and mixtures thereof.

The polyether type polyol may be a polypropylene glycol, a polyethylene glycol, a polypropylene glycol glycerol triol, a polyethylene glycol glycerol triol, or a polytetrahydrofuran.

The polyester type polyol may be a polycaprolactone, a polyester of fatty acid dimers comprising 34 to 36 carbon atoms, a polyadipate polyester or a polyphthalate polyester.

The polycarbonate polyol may be a 1,6-hexanediol polycarbonate.

Preferably, the polyol containing between 1.5 and 3 OH functions and having a molecular weight between 900 and 3,000 g/mol used to form the masked prepolymer is a polytetrahydrofuran, a 1,6-hexanediol polycarbonate, a polyester of fatty acid dimers comprising 34 to 36 carbon atoms, a polycaprolactone or a hydroxylated polybutadiene.

According to a particular embodiment, directed toward the preparation of a waterproof coating, the ready-to-use liquid composition according to the invention comprises:
- 2% to 15% of masked polyisocyanate;
- 30% to 80% and preferentially from 25% to 65% by weight of prepolymer;
- 0 to 40% and preferentially from 20% to 30% by weight of plasticizer;
- 0 to 5% and preferentially from 0.02% to 1.5% by weight of catalyst;
- 0 to 20%, preferably from 0 to 10% and even more preferentially from 0 to 2% by weight of solvent;
- 0 to 50%, preferably 0 to 40% and even more preferentially 0 to 30% by weight of fillers;

the percentages being weight percentages relative to the total weight of the composition.

According to another particular embodiment, directed toward the preparation of a primer, the ready-to-use liquid composition according to the invention comprises:
- 2% to 90% and preferentially from 5% to 70% of masked polyisocyanate;
- 10% to 80% and preferentially from 15% to 65% by weight of prepolymer;
- 0 to 40% and preferentially from 20% to 30% by weight of plasticizer, preferably of polymerizable plasticizer;
- 0 to 5% and preferentially from 0.02% to 1.5% by weight of catalyst;
- 0 to 80%, preferably from 2% to 30% and even more preferentially from 5% to 20% of solvent;
- 0 to 50%, preferably 0 to 40% and even more preferentially 0 to 30% of fillers;

the percentages being weight percentages relative to the total weight of the composition.

In the above compositions, the prepolymer is either a standard prepolymer or a mixture of standard prepolymer and of masked prepolymer.

In the above compositions, use may also be made, as plasticizer, of a polymerizable plasticizer which is the reaction product of:
- an alcohol type compound containing a hydrocarbon chain comprising and/or being substituted with an aromatic ring and/or an aliphatic ring and/or said hydrocarbon chain of the alcohol type compound is substituted with at least two hydrocarbon chains which may comprise an unsaturation and wherein said alcohol type compound has an —OH number between 0.8% and 2.5%; with
- a polyisocyanate comprising 2.1 to 3.2 isocyanate functions and preferably 2.5 to 3.1 isocyanate functions;

as described in patent application PCT/FR2012/052369 filed on Oct. 18, 2012 in the name of the Applicant, which is incorporated by reference.

According to a particular embodiment, these compositions do not contain any masked polyisocyanate, but at least part of the prepolymer is a masked prepolymer which is the reaction product of a polyol with a masked polyisocyanate having a number of isocyanate functions between 1.5 and 2.2 as described above.

According to another particular embodiment, these compositions comprise both the masked polyisocyanate and the masked prepolymer as defined above.

These compositions are stable and have low toxicity since they comprise less than 5%, preferably less than 4%, more preferentially less than 3%, even more preferentially less than 2% and even more preferentially less than 1% by weight of free diisocyanate monomers. They may be sold without the labeling "R40: suspected carcinogenic effect—insufficient proof", given their low free diisocyanate monomers content.

The compositions according to the invention are also stable on storage, given that the masked polyisocyanate and/or the masked prepolymer described above are advantageously less reactive than standard polyisocyanates and/or standard prepolymers.

As the masked polyisocyanate described above is a good compatibilizer for hydrocarbon fillers, such as natural or synthetic bitumen, and for prepolymers, its use in bituminous polyurethane resin compositions makes it possible to reduce the amount of exogenous plasticizers and thus to avoid the exudation of exogenous plasticizer at the surface of the coating formed.

When the compositions do not comprise any solvent, they may be used in interiors even in countries having the strictest legislation.

According to an advantageous embodiment, the present compositions contain little or no solvent. The term "little solvent" means a solvent content of less than 10%, preferably less than 5% and more preferentially less than 2% by weight.

According to a preferred embodiment, the compositions according to the invention do not contain any solvent.

Use

An object of the invention is also the use of the masked polyisocyanate as defined previously and wherein the number of isocyanate functions is between 1.5 and 2.2, for the preparation of a masked prepolymer, by reaction of said masked polyisocyanate with a polyol containing between 1.5 and 3 OH functions and having a molecular weight between 900 and 3000 g/mol, preferably between 1,000 and 2,800 g/mol and more preferentially between 1,500 and 2,500 g/mol, in a ratio such that the number of NCO functions of the polyisocyanate relative to the number of OH functions of the polyol is from 1.5 to 2.5 approximately.

An object of the invention is also the use of the masked polyisocyanate and/or of the masked prepolymer as defined previously in polyurethane resin compositions, preferably in stable one-component polyurethane resin compositions. The use of the masked polyisocyanate and/or of the masked prepolymer in polyurethane resin compositions makes it possible to obtain a free diisocyanate monomers content of less than 5%, preferably less than 4%, more preferentially less than 3%, even more preferentially less than 2% and even more preferentially less than 1% by weight of free diisocyanate monomers. Furthermore, the use of the masked polyisocyanate in polyurethane resin compositions improves the compatibilization between the hydrocarbon fillers and the prepolymers, which makes it possible to obtain a stable composition.

The invention also relates to the use of the composition according to the invention for making coatings, especially waterproof coatings, which do not have any surface defects, such as bubbles, and which are strong enough for exterior use, unprotected and optionally traffic-bearing. The obtained coatings have an entirely satisfactory water uptake, i.e. less than 8% after 28 days of immersion in water at 20° C. The coatings obtained by the use of the composition according to the invention can cover horizontal, oblique, vertical or rough surfaces and/or surfaces comprising singular points.

The non-bituminous polyurethane resin compositions are preferentially used for waterproofing exterior traffic-bearing horizontal surfaces, such as balconies, stadium terraces, parking lots, building courtyards, etc.

The bituminous polyurethane resin compositions are preferentially used for making flashings, i.e. for making a waterproof coating between a bituminous surface and a vertical wall or a singular point, or for renovating roofs.

The invention will be described in greater detail with the aid of the following examples, which are given for purely illustrative purposes.

EXAMPLES

In the examples, the parts are expressed on a weight basis. The viscosities are measured using a Brookfield viscometer, spindle 5 or 6, speed 20 rpm at 23° C., less than one week after manufacturing the product or the composition.

In the examples, the following commercial products are used:

Suprasec® 2385: modified MDI containing 2 isocyanate functions, sold by Huntsman.

Suprasec® 5025: polymeric MDI containing 2.7 isocyanate functions, sold by Huntsman.

Ruetasolv® Di: diisopropylnaphthalene plasticizing oil sold by RKS.

Sovermol® 920: polycarbonate polyol polyether containing 2 OH functions, sold by Cognis.

Voranol® 2000: polypropylene glycol with a molecular weight of 2,000 g/mol (CAS 025322-69-4) sold by Dow Chemical.

Polybutadiene 3000: polybutadiene diol of molar mass 3,000 g/mol.

Desmodur® L75: aromatic polyisocyanate based on TDI at 75% in ethyl acetate, sold by Bayer.

PolyTHF® 2000: polytetrahydrofuran containing 2 NCO functions and having a molecular weight of 2,000 g/mol sold by BASF.

Jeffcat® DMDLS: tertiary amine sold by Huntsman.

PTSI: para-toluenesulfonyl isocyanate.

Example 1

Preparation of a Masked Polyisocyanate 10.2 parts of hexanol are gradually added to 37 parts of Suprasec® 5025 so that the temperature remains below 50° C.

When the addition of hexanol is complete, the mixture is allowed to return to room temperature.

A viscosity of 5,000 centipoises is then obtained, as measured with a Brookfield viscometer at 23° C., with an R5 module at a speed of 20 rpm.

Example 2

Preparation of a Masked Polyisocyanate 12 parts of 2-ethylhexanol are gradually added to 37 parts of Suprasec® 5025 in 32.3 parts of Ruetasolv® Di, so that the temperature remains below 50° C.

When the addition of 2-ethylhexanol is complete, the mixture is allowed to return to room temperature.

A viscosity of 1,000 centipoises is then obtained, as measured with a Brookfield viscometer at 23° C., with an R5 module at a speed of 20 rpm.

Example 3

Preparation of a Masked Polyisocyanate 100 parts of hexanol are gradually added to 900 parts of Desmodur® L75 so that the temperature remains below 50° C.

When the addition of hexanol is complete, the mixture is allowed to return to room temperature.

A viscosity of 2,600 centipoises is then obtained, as measured with a Brookfield viscometer at 23° C., with an R5 module at a speed of 20 rpm.

Example 4

Preparation of a Masked Polyisocyanate 130 parts of 2-ethylhexanol are gradually added to 37 parts of Suprasec® 5025 in 30 parts of butyl acetate, so that the temperature remains below 50° C.

When the addition of 2-ethylhexanol is complete, the mixture is allowed to return to room temperature.

A viscosity of 750 centipoises is then obtained, as measured with a Brookfield viscometer at 23° C., with an R5 module at a speed of 20 rpm.

Example 5

Preparation of a Prepolymer with a Masked Polyisocyanate

A prepolymer is prepared by reacting 100 parts of PolyTHF® 2000 and 75 parts of the masked polyisocyanate prepared in example 1. The mixture is stirred at 70° C. for 1 hour 15 minutes.

The free diisocyanate monomers content is less than 5%.

Example 6

Preparation of a Prepolymer with a Masked Polyisocyanate

A prepolymer is prepared by reacting 200 parts of Sovermol® 920, 45 parts of Suprasec® 2385 and 180 parts of the masked polyisocyanate prepared in example 2. The mixture is stirred at 70° C. for 1 hour 15 minutes.

The free diisocyanate monomers content is 4.5%.

Example 7

Preparation of a Prepolymer with a Masked Polyisocyanate

A prepolymer is prepared by reacting 3,000 parts of polybutadiene 3000, 135 parts of 1,4-butanediol, 540 parts of Suprasec® 2385 and 800 parts of the masked polyisocyanate prepared in example 4. The mixture is stirred at 70° C. for 1 hour 15 minutes.

The free diisocyanate monomers content is less than 5%.

Example 8

Primer Composition (Comparative)

A prepolymer is prepared by reacting 100 parts of Voranol® 2000 and 54 parts of Suprasec® 2385. The mixture is stirred at 80° C. for 2 hours.

The following primer formulation is then prepared:
154 parts of the preceding prepolymer,
20 parts of Suprasec® 2385,
40 parts of xylene.

The composition may be applied as a primer.

The composition prepared has a Brookfield viscosity (spindle 5) at 23° C. of 400 centipoises.

The composition is stored for 4 months at 20° C. After 4 months, the composition rapidly becomes homogeneous when it is mixed with a stick, and no phase separation is observed.

The free diisocyanate monomers content is greater than 5%. Such a product is labeled "R 40: suspected carcinogenic effect—insufficient proof" in Europe and "hazardous" in Asia.

Example 9

Primer Composition

A prepolymer is prepared by reacting 100 parts of Voranol® 2000 and 91 parts of the masked polyisocyanate prepared in example 1. The mixture is stirred at 80° C. for 2 hours.

A primer solution is prepared by mixing:
154 parts of the preceding prepolymer,
35 parts of the masked polyisocyanate prepared in example 1,
70 parts of xylene.

This one-component composition is stable and may be applied with a roller to make an exterior primer.

The free diisocyanate monomers content is less than 1%. Such a composition may be sold without the labeling "R40: suspected carcinogenic effect—insufficient proof".

Example 10

Bituminous Composition

The cut-back 160/220+PTSI is prepared in a reactor. 80 parts of molten 160/220 grade bitumen are first heated to 110° C., and 20 parts of toluene are incorporated therein. The mixture is stirred at 1,200 rpm for 4 minutes and is allowed to return to room temperature. 1 part of PTSI is then added and the mixture is stirred at 1,200 rpm for 4 minutes.

The following ingredients are mixed in a reactor so as to form the polyurethane resin composition:
100 parts of the masked prepolymer synthesized in example 5,
100 parts of cut-back 160/220+PTSI synthesized above, and this mixture is stirred for 3 minutes.
15 parts of xylene,
0.2 part of Jeffcat® DMDLS.

The mixture is stirred for 3 minutes. A liquid composition is obtained, which may be used to make a waterproof roof coating. The composition has a free diisocyanate monomers content of less than 1%. Such a composition may be sold without the labeling "R40: suspected carcinogenic effect—insufficient proof".

Example 11

Bituminous Composition

The cut-back 160/220+PTSI is prepared in a reactor. 80 parts of molten 160/220 grade bitumen are first heated to 110° C., and 20 parts of toluene are incorporated therein. The mixture is stirred at 1,200 rpm for 4 minutes and is allowed to return to room temperature. 1 part of PTSI is then added and the mixture is stirred at 1,200 rpm for 4 minutes.

The following ingredients are mixed in a reactor so as to form the polyurethane resin composition:
500 parts of the masked prepolymer synthesized in example 7,
500 parts of cut-back 160/220+PTSI synthesized above, and this mixture is stirred for 3 minutes.
1 part of Jeffcat® DMDLS.

The mixture is stirred for 3 minutes. A liquid composition is obtained, which may be used to make a waterproof roof coating. The composition has a free diisocyanate monomers content of less than 1%. Such a composition may be sold without the labeling "R40: suspected carcinogenic effect—insufficient proof".

The invention claimed is:

1. A stable, liquid polyurethane composition which comprises:
at least one masked polyisocyanate corresponding to the following formula:

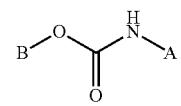

wherein:
B represents alkyl,
A represents a group comprising a number of isocyanate functions between 1.5 and 2.2;
at least one prepolymer which is the reaction product of polyol or of a mixture of polyols containing a number of OH functions between 1.5 and 3 with a polyisocyanate or a mixture of polyisocyanates containing a number of NCO functions between 1.6 and 3, in a ratio such that the number of NCO functions of the polyisocyanate or of the polyisocyanate mixture relative to the number of OH functions of the polyol or mixture of polyols is from 1.5 to 2.5 approximately;
optionally a plasticizer;
optionally a catalyst;

optionally solvent and/or diluent;
optionally a filler.

2. A stable, liquid polyurethane composition which comprises:
at least one masked prepolymer formed by reaction between:
a polyol containing between 1.5 and 3 OH functions and having a molecular weight between 900 and 3,000 g/mol; and
a masked polyisocyanate corresponding to the following formula

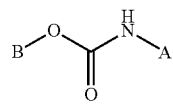

wherein:
B represents alkyl,
A represents a group comprising a number of isocyanate functions between 1.5 and 2.2;
in a ratio such that the number of NCO functions of the masked polyisocyanate relative to the number of OH functions of the polyol or mixture of polyols is from 1.5 to 2.5 approximately;
optionally a polyisocyanate containing between 1.5 and 3 NCO functions;
optionally a plasticizer;
optionally a catalyst;
optionally solvent and/or diluent.

3. The stable, liquid polyurethane composition according to claim 2, further comprising a masked polyisocyanate corresponding to the following formula:

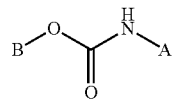

wherein:
B represents alkyl,
A represents a group comprising a number of isocyanate functions between 1.5 and 2.2.

4. The stable, liquid polyurethane composition according to claim 1, wherein said composition comprises less than 5% by weight of free diisocyanate monomers.

5. The stable, liquid polyurethane composition according to claim 2, wherein the polyol used to form the masked prepolymer is a polyether, polyester, polybutadiene or polycarbonate type polyol, and mixtures thereof.

6. The stable, liquid polyurethane composition according to claim 2, wherein the polyol is a polytetrahydrofuran, a 1,6-hexanediol polycarbonate, a polyester of fatty acid dimers comprising 34 to 36 carbon atoms, a polycaprolactone or a hydroxylated polybutadiene.

7. The stable, liquid polyurethane composition according to claim 1, wherein B represents an optionally unsaturated $C_2$-$C_{20}$ alkyl.

8. The stable, liquid polyurethane composition according to claim 1, wherein the "group" of A is:
a polymer chain (originating from a polymeric MDI) corresponding to formula (A1):

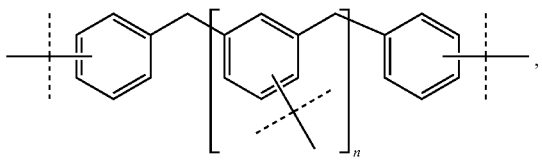

a radical corresponding to formula (A2) or to a related radical of a TDI trimer:

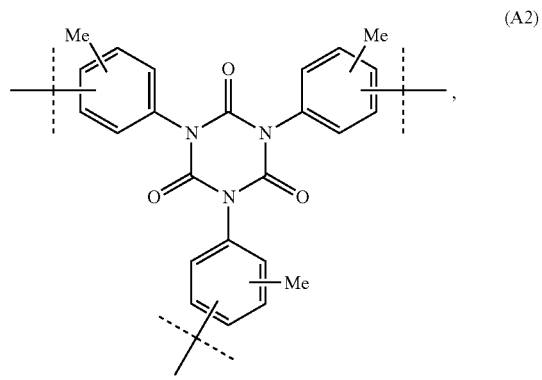

a radical corresponding to one of the formulae (A3) and/or (A4) or to a related radical of an HDI trimer:

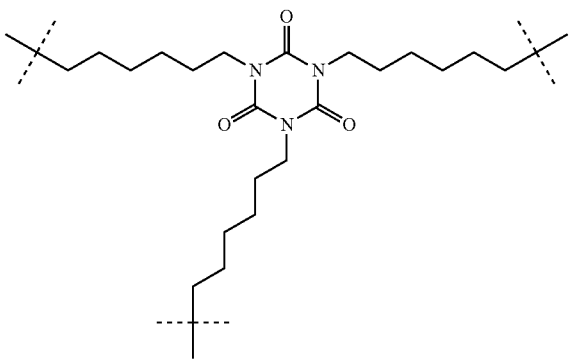

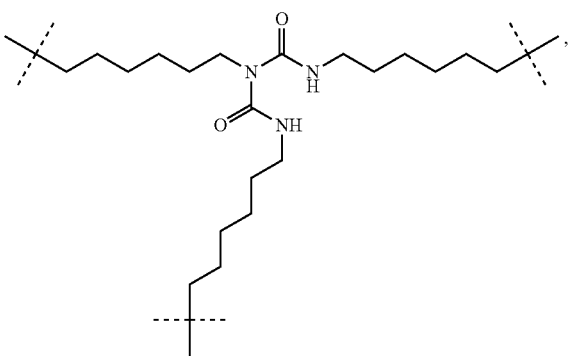

a radical corresponding to formula (A5) or to a related radical of an IPDI trimer:

(A5)

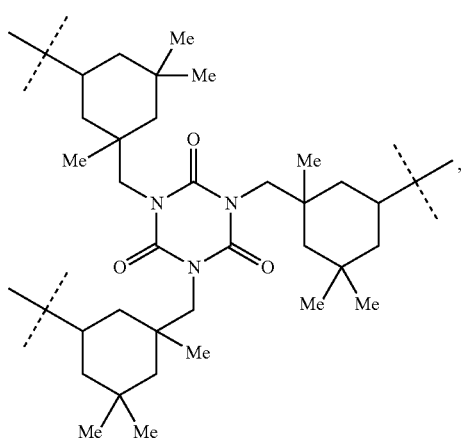

wherein each dashed line represents a point of attachment to a NCO function or to the group —NHCOO—B of the masked polyisocyanate and on condition that there is at least one dashed line that is a point of attachment to the group —NHCOO—B and that the remaining lines represent a point of attachment to a NCO function.

9. A process for the preparation of a stable, liquid polyurethane resin composition comprising introducing the masked polyisocyanate according to claim 1 in said stable, liquid polyurethane resin composition.

10. The stable, liquid polyurethane composition according to claim 2, wherein said composition comprises less than 5% by weight of free diisocyanate monomers.

11. The stable, liquid polyurethane composition according to claim 2, wherein B represents an optionally unsaturated $C_2$-$C_{20}$ alkyl.

12. The stable, liquid polyurethane composition according to claim 2, wherein the "group" of A is:
a polymer chain (originating from a polymeric MDI) corresponding to formula (A1):

(A1)

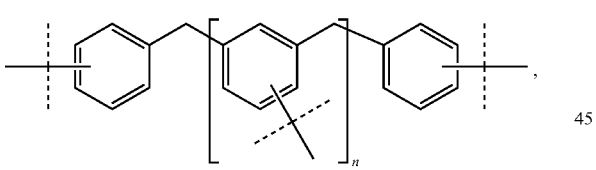

a radical corresponding to formula (A2) or to a related radical of a TDI trimer:

(A2)

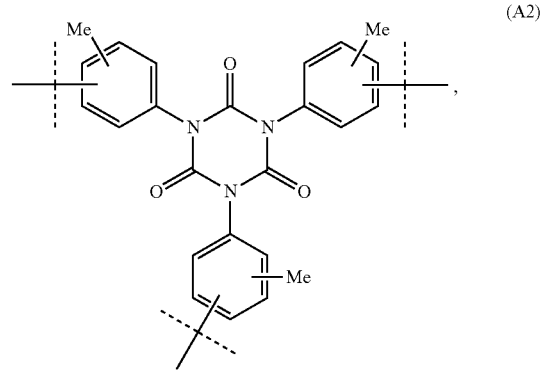

a radical corresponding to one of the formulae (A3) and/or (A4) or to a related radical of an HDI trimer:

(A3)

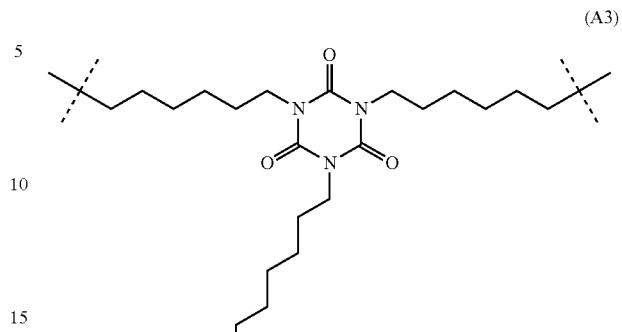

(A4)

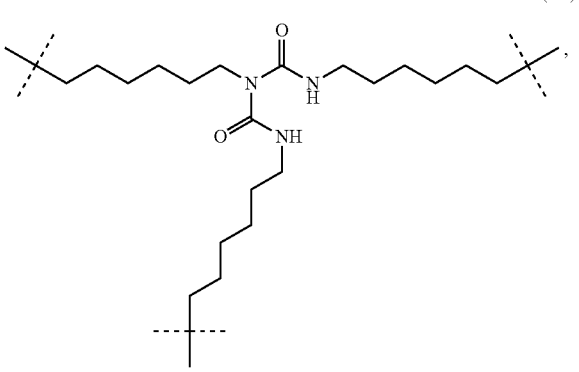

a radical corresponding to formula (A5) or to a related radical of an IPDI trimer:

(A5)

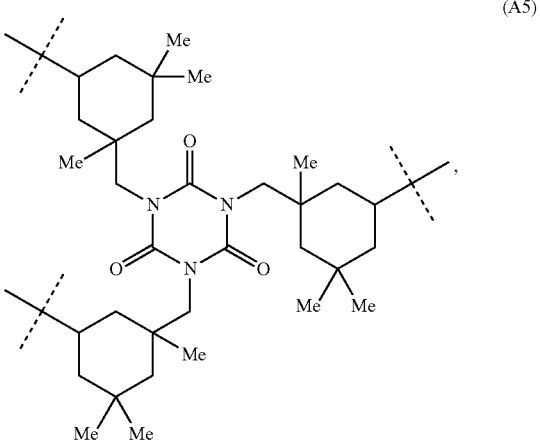

wherein each dashed line represents a point of attachment to a NCO function or to the group —NHCOO—B of the masked polyisocyanate and on condition that there is at least one dashed line that is a point of attachment to the group —NHCOO—B and that the remaining lines represent a point of attachment to a NCO function.

13. A process for the preparation of a stable, liquid polyurethane resin composition comprising introducing the masked prepolymer according to claim 2 in said stable, liquid polyurethane resin composition.

* * * * *